(12) United States Patent
Mitsuhashi (10) Patent No.: US 8,366,608 B2
(45) Date of Patent: Feb. 5, 2013

(54) IN-VIVO INFORMATION ACQUIRING SYSTEM AND BODY-INSERTABLE APPARATUS

(75) Inventor: Kei Mitsuhashi, Nishitokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1014 days.

(21) Appl. No.: 12/324,444

(22) Filed: Nov. 26, 2008

(65) Prior Publication Data

US 2009/0137873 A1 May 28, 2009

(30) Foreign Application Priority Data

Nov. 28, 2007 (JP) ................................. 2007-307876

(51) Int. Cl.
*A61B 1/06* (2006.01)
*A61B 1/04* (2006.01)
(52) U.S. Cl. ........................................ 600/160; 600/109
(58) Field of Classification Search .................. 600/103, 600/117–118, 109, 160
See application file for complete search history.

(56) References Cited

U.S. PATENT DOCUMENTS

| | | | |
|---|---|---|---|
| 6,904,308 B2 | 6/2005 | Frisch et al. | |
| 2005/0025368 A1* | 2/2005 | Glukhovsky | 382/236 |
| 2005/0049461 A1 | 3/2005 | Honda et al. | |
| 2005/0065441 A1* | 3/2005 | Glukhovsky | 600/476 |
| 2007/0156016 A1* | 7/2007 | Betesh et al. | 600/102 |
| 2007/0206092 A1* | 9/2007 | Skala | 348/77 |
| 2007/0255099 A1* | 11/2007 | Yokoi et al. | 600/109 |
| 2007/0287891 A1* | 12/2007 | Horn | 600/300 |
| 2008/0004503 A1* | 1/2008 | Nisani et al. | 600/300 |
| 2008/0103363 A1* | 5/2008 | Levy et al. | 600/160 |
| 2009/0046821 A1* | 2/2009 | Shigemori et al. | 375/371 |
| 2009/0313672 A1* | 12/2009 | Nisani et al. | 725/114 |

FOREIGN PATENT DOCUMENTS

| | | |
|---|---|---|
| EP | 1 492 352 A2 | 12/2004 |
| JP | S63-49128 A | 3/1988 |
| JP | H06-335449 A | 12/1994 |
| JP | H09-154813 A | 6/1997 |
| JP | H11-164831 A | 6/1999 |
| JP | H11-298907 A | 10/1999 |

(Continued)

OTHER PUBLICATIONS

Extended European Search Report from corresponding European Patent Application Publication No. EP 08 85 5729.3 dated Dec. 12, 2011.

(Continued)

*Primary Examiner* — Philip R Smith
(74) *Attorney, Agent, or Firm* — Scully, Scott, Murphy & Presser, P.C.

(57) ABSTRACT

An in-vivo information acquiring system includes a body-insertable apparatus that transmits a wireless signal containing an in-vivo image, and a receiving apparatus that receives the wireless signal. The body-insertable apparatus includes an imaging unit, a selecting unit, and a transmitting unit. The imaging unit captures in-vivo images. The selecting unit selects an in-vivo image to be added with unique information from the in-vivo images. The transmitting unit additionally arranges an identification signal, which is written according to a signal sequence rule of synchronization signals added to scanning line information about the in-vivo image selected by the selecting unit, in a position corresponding to positions in which the synchronization signals are arranged, adds unique information corresponding to the identification information after the identification information, and transmits the in-vivo image added with the unique information.

5 Claims, 11 Drawing Sheets

FOREIGN PATENT DOCUMENTS

| | | |
|---|---|---|
| JP | 2001-231186 | 8/2001 |
| JP | 2001-245844 A | 9/2001 |
| JP | 2003-019105 A | 1/2003 |
| JP | 2003-19111 | 1/2003 |
| JP | 2003-135389 A | 5/2003 |
| JP | 2004-305371 | 11/2004 |
| JP | 2005-020755 | 1/2005 |
| WO | WO 01/35813 A1 | 5/2001 |
| WO | WO 03/010967 A1 | 2/2003 |
| WO | WO 2004/112593 A1 | 12/2004 |

OTHER PUBLICATIONS

Decision of a Patent Grant dated Aug. 21, 2012 in corresponding Japanese Patent Application No. 2007-307876.

* cited by examiner

| FRAME | TRANSMISSION OF UNIQUE INFORMATION | INFORMATION TO BE TRANSMITTED ||||| T1
| | | WHITE BALANCE COEFFICIENT | PRODUCT SERIAL NUMBER | PRODUCT VERSION INFORMATION | PRODUCT TYPE | LIGHT EMISSION TIME |
|---|---|---|---|---|---|---|
| 1 | NECESSARY | ○ | ○ | ○ | ○ | ○ |
| 2 | NECESSARY | ○ | ○ | ○ | ○ | ○ |
| 3 | NECESSARY | ○ | ○ | ○ | ○ | ○ |
| 4 | UNNECESSARY | — | — | — | — | — |
| 5 | UNNECESSARY | — | — | — | — | — |
| 6 | NECESSARY | — | ○ | — | — | ○ |
| 7 | UNNECESSARY | — | — | — | — | — |
| 8 | UNNECESSARY | — | — | — | — | — |
| 9 | NECESSARY | — | ○ | — | — | — |
| 10 | NECESSARY | ○ | ○ | — | — | ○ |
| 11 | UNNECESSARY | — | — | — | — | — |
| ⋮ | ⋮ | ⋮ | ⋮ | ⋮ | ⋮ | ⋮ |

| | | | |
|---|---|---|---|
| G11a | PREAMBLE | ID | UNIQUE INFORMATION } L11-S |
| | | VD | IMAGE DATA } L11-1 |
| | | HD | IMAGE DATA } L11-2 |
| | | HD | IMAGE DATA } L11-3 |
| | | ⋮ | ⋮ |
| | | HD | IMAGE DATA } L11-n |
| G12 | PREAMBLE | VD | IMAGE DATA |
| | | HD | IMAGE DATA |
| | | HD | IMAGE DATA |
| | | ⋮ | ⋮ |
| | | HD | IMAGE DATA |
| G13 | PREAMBLE | VD | IMAGE DATA |
| | | HD | IMAGE DATA |
| | | HD | IMAGE DATA |
| | | ⋮ | ⋮ |
| | | HD | IMAGE DATA |
| ⋮ | | | |
| G1m | PREAMBLE | VD | IMAGE DATA |
| | | HD | IMAGE DATA |
| | | HD | IMAGE DATA |
| | | ⋮ | ⋮ |
| | | HD | IMAGE DATA |

| FRAME | ... | 10 | 11 | 12 | 13 | 14 | ... |
|---|---|---|---|---|---|---|---|
| LED EMISSION TIME [msec] | ... | 3 | 5 | 5 | 5 | 8 | ... |
| TRANSMISSION OF UNIQUE INFORMATION | ... | — | ○ | — | — | ○ | ... |

| FRAME | ... | 10 | 11 | 12 | 13 | 14 | ... |
|---|---|---|---|---|---|---|---|
| LED EMISSION TIME [msec] | ... | 3 | 5 | 5 | 5 | 8 | ... |
| DIFFERENCE VALUE FROM PREVIOUS LED EMISSION TIME | ... | 0 | 2 | 0 | 0 | 3 | ... |
| TRANSMISSION OF UNIQUE INFORMATION | ... | — | ○ | — | — | ○ | ... |

Y15　　　　　Y16

IN-VIVO INFORMATION ACQUIRING SYSTEM AND BODY-INSERTABLE APPARATUS

CROSS-REFERENCE TO RELATED APPLICATIONS

This application is based upon and claims the benefit of priority from Japanese Patent Application No. 2007-307876, filed Nov. 28, 2007, the entire contents of which are incorporated herein by reference.

BACKGROUND OF THE INVENTION

1. Field of the Invention

The present invention relates to an in-vivo information acquiring system that acquires in-vivo images and a body-insertable apparatus.

2. Description of the Related Art

Recently, in the field of endoscopes, swallowable capsule endoscopes have been developed. A swallowable capsule endoscope, which has an imaging function and a wireless function, is introduced from the mouse of a patient for observing the body cavity. Until being naturally excreted from the body, the capsule endoscope sequentially captures in-vivo images while moving through the organs including the esophagus, the stomach, and the small intestine depending on peristalsis (see, for example, Japanese Patent Application Laid-open Nos. 2003-019111 and 2001-231186). While the capsule endoscope moves through the body cavity, image data about the in-vivo images captured by the capsule endoscope is wirelessly transmitted to the outside sequentially, and stored in a memory provided to an external receiving apparatus. A doctor or a nurse displays the image data stored in the memory on a display to diagnose the patient.

SUMMARY OF THE INVENTION

An in-vivo information acquiring system according to an aspect of the present invention includes a body-insertable apparatus. The body-insertable apparatus is introduced into a subject, and transmits a wireless signal containing an in-vivo image to the outside of the subject. The in-vivo information acquiring system also includes a receiving apparatus that receives the wireless signal transmitted from the body-insertable apparatus. The body-insertable apparatus also includes an imaging unit that captures in-vivo images; a selecting unit that selects an in-vivo image to be added with unique information among the in-vivo images captured by the imaging unit; and a transmitting unit that additionally arranges an identification signal, which is written according to a signal sequence rule of synchronization signals added to scanning line information about the in-vivo image selected by the selecting unit, in a position corresponding to positions in which the synchronization signals are arranged, adds unique information corresponding to the identification information after the identification information, and transmits the in-vivo image added with the unique information.

A body-insertable apparatus according to another aspect of the present invention includes an imaging unit that captures in-vivo images; a selecting unit that selects an in-vivo image to be added with unique information among the in-vivo images captured by the imaging unit; and a transmitting unit that additionally arranges an identification signal, which is written according to a signal sequence rule of synchronization signals added to scanning line information about the in-vivo image selected by the selecting unit, in a position corresponding to positions in which the synchronization signals are arranged, adds unique information corresponding to the identification information after the identification information, and transmits the in-vivo image added with the unique information.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention are explained in detail below with reference to the accompanying drawings.

Figure 1:
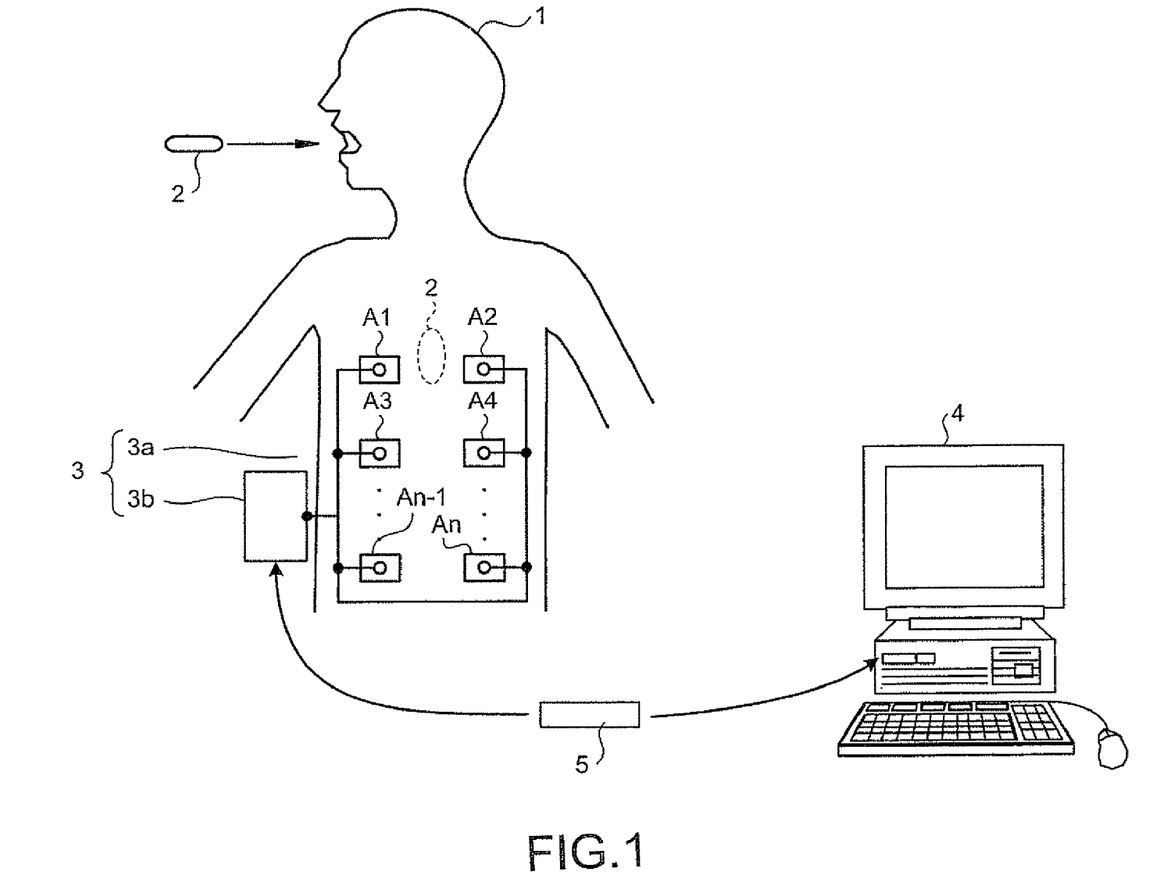
FIG. 1 is a schematic diagram of a configuration of an in-vivo information acquiring system according to a first embodiment of the preset invention.

A wireless in-vivo information acquiring system according to a first embodiment is explained below. FIG. 1 is a schematic diagram of a configuration of the in-vivo information acquiring system. The in-vivo information acquiring system includes a single-lens capsule endoscope 2 as an example of a body-insertable apparatus. As shown in FIG. 1, the in-vivo information acquiring system includes the capsule endoscope 2 that is introduced into a subject 1, captures in-vivo images, and wirelessly transmits data such as image signals to a receiving apparatus 3; the receiving apparatus 3 that receives the image data about the in-vivo images wirelessly transmitted from the capsule endoscope 2; an external processing apparatus 4 that displays the in-vivo images based on the image signals received by the receiving apparatus 3; and a portable recording medium 5 used for exchanging data between the receiving apparatus 3 and the processing apparatus 4.

The receiving apparatus 3 includes a wireless unit 3a including a plurality of receiving antennas A1 to An to be attached to the body surface of the subject 1, and a receiving main unit 3b that processes wireless signals received via the receiving antennas A1 to An. The wireless unit 3a and the receiving main unit 3b are connectable via, for example, a connector. The receiving antennas A1 to An are connected to, for example, a jacket to be worn by the subject 1. In this case, by wearing the jacket, the subject 1 is attached with the receiving antennas A1 to Ab. The receiving antennas A1 to An can be configured to be detachable from the jacket.

The processing apparatus 4 processes the in-vivo images captured by the capsule endoscope 2, and displays the processed in-vivo images. The processing apparatus 4 is configured as, for example, a workstation that displays images based on data from the portable recording medium 5. Specifically, the processing apparatus 4 can be configured to directly display images on a cathode ray tube (CRT) display or a liquid crystal display (LCO) or can be configured to output the images to a medium, such as a printer.

The portable recording medium 5 is, for example, a CompactFlash® memory. The portable recording medium 5 is attachable to the receiving main unit 3b and the processing apparatus 4, and outputs or stores information while being inserted to the receiving main unit 3b or the processing apparatus. Specifically, the portable recording medium 5 is inserted into the receiving main unit 3b while the capsule endoscope 2 moves thorough the body cavity of the subject 1, and the data transmitted from the capsule endoscope 2 is stored in the portable recording medium 5. After the capsule endoscope 2 is excreted from the subject 1, i.e., after the capsule endoscope 2 finishes capturing in-vivo images, the portable recording medium 5 is detached from the receiving main unit 3b and inserted into the processing apparatus 4 and the processing apparatus 4 reads the data from the portable recording medium 5. Because the portable recording medium 5 is used to exchange data between the receiving main unit 3b and the image processing apparatus 4, the subject 1 can move freely while in-vivo images are captured. The use of the portable recording medium 5 also shortens the time necessary for exchanging data between the receiving main unit 3b and the image processing apparatus 4. Instead of the portable recording medium 5, a storage device built in the receiving apparatus 3 and configured to be wired or wirelessly connected to the image processing apparatus 4 may be used to exchange data between the receiving main unit 3b and the processing apparatus 4.

Figure 2:
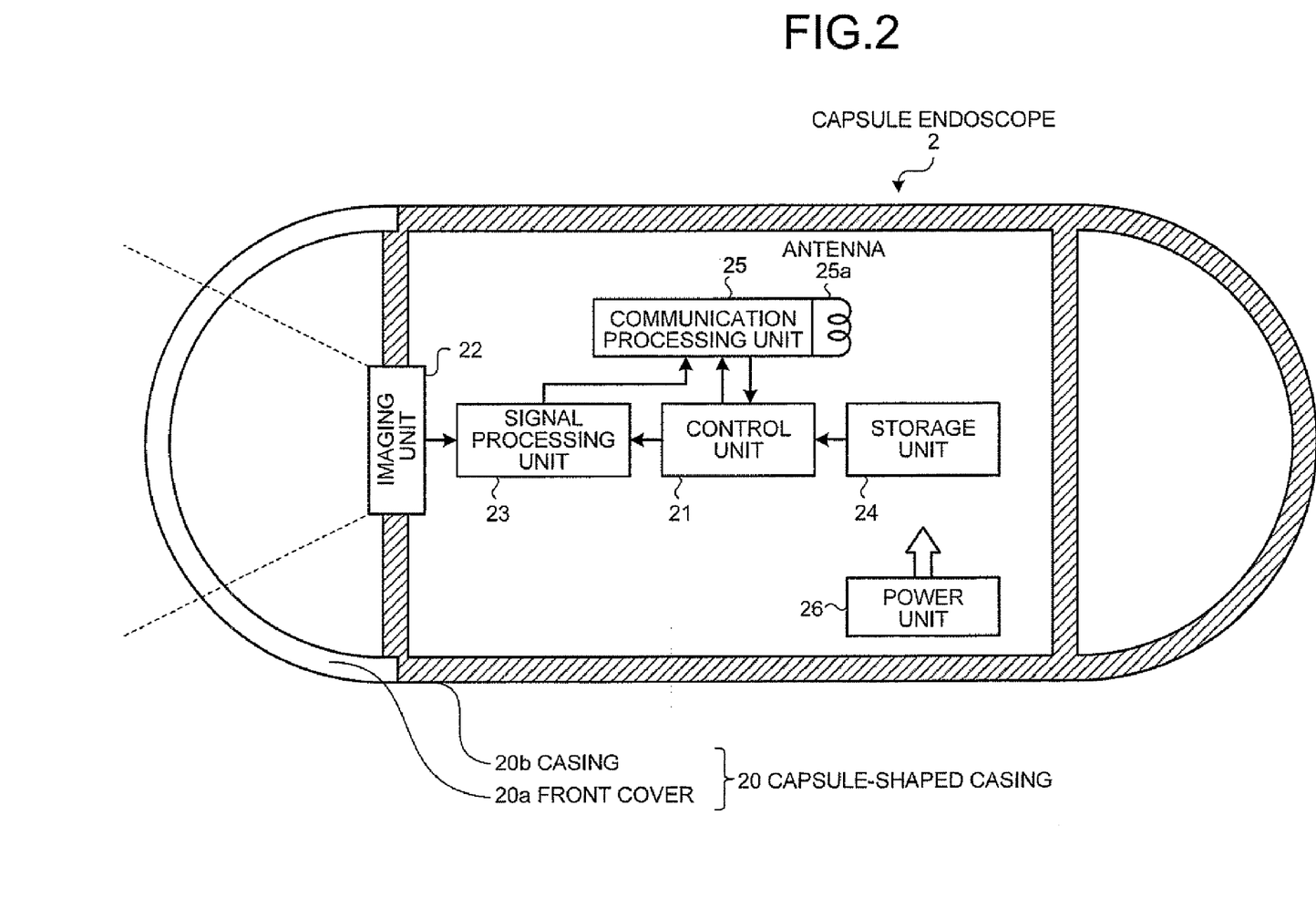
FIG. 2 is a block diagram of a configuration of a capsule endoscope shown in FIG. 1.

A configuration of the capsule endoscope 2 is explained in detail below. FIG. 2 is a schematic diagram of a configuration of the capsule endoscope 2. As shown in FIG. 2, the capsule endoscope 2 includes a capsule-shaped casing 20 containing an imaging unit 22 that captures in-vivo images of the subject 1 and a power unit 26 that supplies power to each unit of the capsule endoscope 2. As shown in FIG. 2, the capsule endoscope 2 includes the one single imaging unit 22. Alternatively, the capsule endoscope 2 may include a plurality of imaging units 22.

The capsule-shaped casing 20 includes a transparent dome-shaped front cover 20a that covers the imaging unit 22, and a casing 20b that is provided water-tightly together with the front cover 20a. The capsule-shaped casing 20 also has a size that allows the subject 1 to swallow it from his/her mouse. The front cover 20a is attached to one end of the casing 20b. The casing 20b is made of a colored material through which a visible light cannot pass. The casing 20b contains a control unit 21 that controls driving of each unit of the capsule endoscope 2, and controls inputting of signals to each unit and outputting of signals from each unit; the imaging unit 22; a signal processing unit 23 that processes the images captured by the imaging unit 22; a storage unit 24 that stores information necessary for wireless communication; a communication processing unit 25 that modulates various types of signals to be transmitted to the processing apparatus 4, and demodulates a wireless signal received via an antenna 25a; and the power unit 26. The communication processing unit 25 includes the antenna 25a which is, for example, a coil antenna, for exchanging wireless signals with an external antenna.

The imaging unit 22 captures in-vivo images of the subject 1. Specifically, the imaging unit 22 includes an optical system including an imaging device, such as a charge coupled device (CCD) type or a complementary metal oxide semiconductor (CMOS) type; a light emitting device, such as a light emitting diode (LED), which illuminates a site whose image is to be captured; and a lens that focuses the light reflected from the site. The imaging unit 22 is fixed to an end of the casing 20b, focuses the light reflected from the site and received via the front cover 20a, thereby capturing an in-vivo image of the subject 1. The optical system has includes lenses designed to have an optical performance suitable for a site for which the capsule endoscope 2 is used, and has a signal processing function. A time in which the LED emits light (hereinafter, "LED emission time") varies depending on a target site to be observed and the distance between the target site and the capsule endoscope 2. For example, if the distance between the target site and the capsule endoscope 2 is long, the LED emission time is long. The imaging unit 22 outputs an LED emission time required for capturing each image to the control unit 21.

The capsule endoscope 2 transmits unique information to be added to image data and independent of line data, which is scanning line information. Specifically, the capsule endoscope 2 additionally arranges an identification signal, which is written in accordance with a signal sequence rule of a vertical synchronization signal and horizontal synchronization signals to be added to the line data, in a position corresponding to the positions in which the vertical synchronization signals and the horizontal synchronization signals are arranged, adds unique information corresponding to the identification signal to the in-vivo image after the identification signal, and transmits the image data added with the unique information. The unique information contains a white balance coefficient, a product serial number, product version information, product type information, and an LED emission time. The white balance coefficient, the product serial number, the product version information, and the product type information are stored in the storage unit 24, and the LED emission time is output from the imaging unit 22 to the signal processing unit 23 each time when an image is captured. It suffices that the information subsequent to the identification signal ID be identified as the unique information based on with the identification signal ID. Therefore, it suffices if the identification signal ID has a signal sequence different from at least those of the vertical synchronization signal and the horizontal synchronization signals.

In the first embodiment, not all images are added with unique information. The capsule endoscope 2 selects image data to be added with unique information, adds unique information to only the selected image data, and transmits the image data added with the unique information.

The control unit 21 selects an image to be added with unique information based on, for example, a pre-set image selection pattern. The image selection pattern indicates which information is to be added with unique information, and it is stored in the storage unit 24.

When the imaging unit 22 outputs an image to be added with unique information, the signal processing unit 23 performs the following under the control of the control unit 21: performing predetermined processing on the image to be added with unique information; additionally arranges an identification signal, which is written according to a signal sequence rule of a vertical synchronization signal and horizontal synchronization signals to be added to line data of the image, in a position corresponding to the positions in which the vertical synchronization signal and the horizontal synchronization signals are arranged; adding unique information corresponding to the identification signal to the image to be added with unique information after the identification signal; and outputting the image added with the unique information to the communication processing unit 25. On the other hand, when the imaging unit 22 outputs an image not to be added with unique information, the signal processing unit 23 performs the predetermined processing on the image without adding unique information to the image, and outputs the processed image to the communication processing unit 25 under the control of the control unit 21. The communication processing unit 25 modulates data output from the signal processing unit 23, and transmits the modulated data to the receiving apparatus 3 via the antenna 25a.

Figure 3:
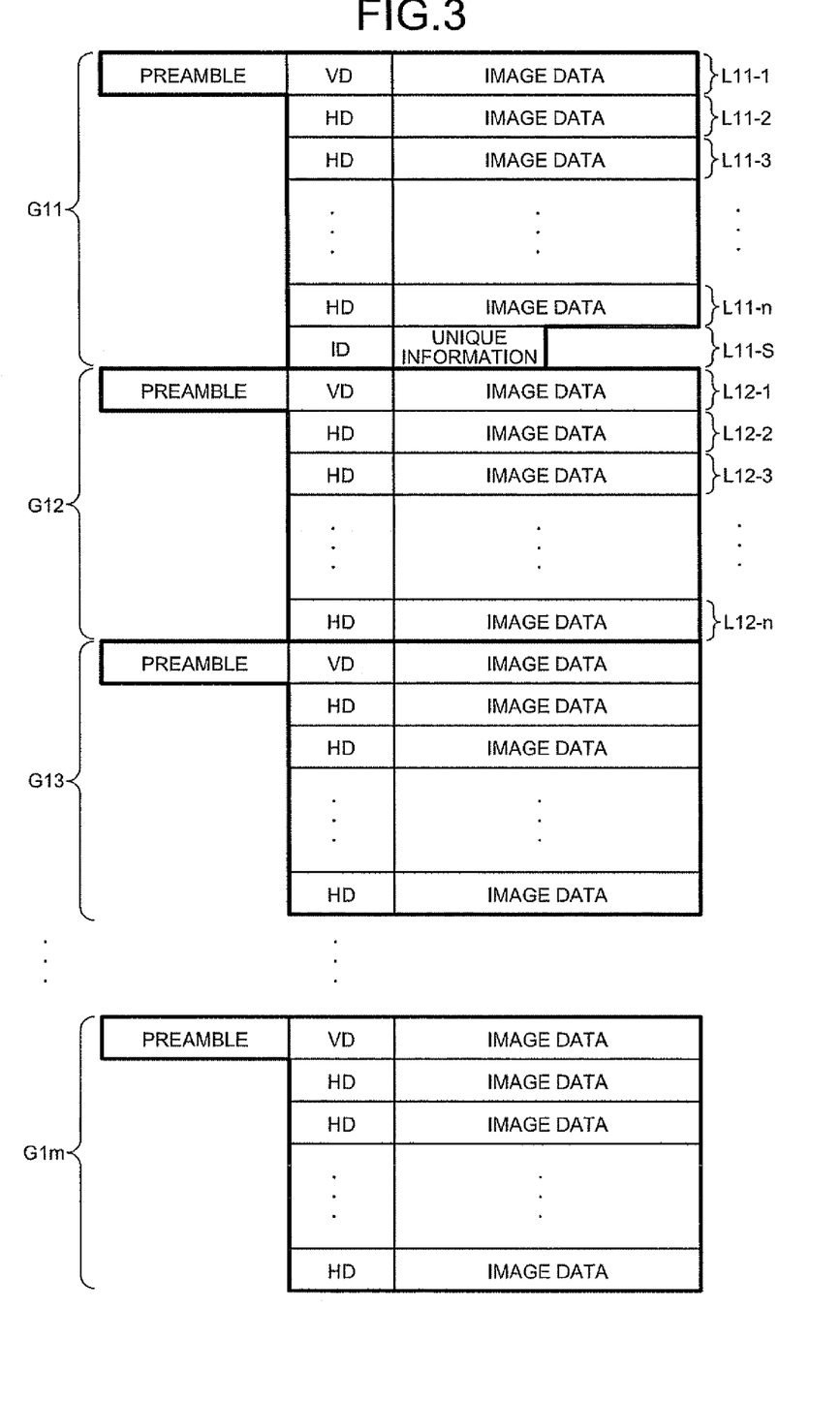
FIG. 3 is a diagram for explaining image signals transmitted from the capsule endoscope shown in FIG. 1.

The data transmitted from the capsule endoscope 2 is explained in detail with reference to FIG. 3. An example is explained where the control unit 21 selects an image G11 of the 11th frame as an image to be added with unique information. First, the signal processing unit 23 processes the image G11 captured by the imaging unit 22 on a line-data basis. Thereafter, as shown in FIG. 3, the signal processing unit 23 adds a vertical synchronization signal VD in addition to a preamble signal representing the top of the image G1 to the top line data L11-1 of the image G11, and adds a horizontal synchronization signal HD to each of the subsequent line data L11-2 to L11-n. Subsequently, the signal processing unit 23 additionally arranges an identification signal ID, which is written in accordance with a signal sequence rule of the vertical synchronization signal VD and the horizontal synchronization signals HD, in a position corresponding to the positions in which the vertical synchronization signal VD and the horizontal synchronization signals HD, and generates a unique information line L11-S to which unique information corresponding to the identification ID is added after the identification ID. The signal processing unit 23 inserts the unique information line L11-S as the line subsequent to the last line data L11-n, and outputs the line data L11-1 to L11-n and the unique information line L11-S as image data corresponding to the image G11 to the communication processing unit 25.

The signal processing unit 23 adds a preamble signal, a vertical synchronization signal VD, and horizontal synchronization signals HD to line data L12-1 to L12-n of an image G12 of the 12th frame other than the images of the 11 frames to be added with unique information as shown in FIG. 3, and transmits the image G12 added with the unique information to the communication processing unit 25. Similarly, the signal processing unit 23 adds a preamble signal, vertical synchronization signals VD, and horizontal synchronization signals HD to line data of images G13 to G1m of the 13th frame and the subsequent frames, and transmits the images G13 to G1m added with the unique information to the communication processing unit 25.

The capsule endoscope 2 does not transmits all types of unique information including a white balance coefficient, a product serial number, product version information, product type information, and an LED emission time. The capsule endoscope 2 selects a type of unique information to be added to image data, adds unique information of only the selected type to an image to be added with unique information, and transmits the image added with the unique information.

The control unit 21 selects the type of unique information to be added to image data based on the pre-set unique information selection pattern. The unique information selection pattern represents which image is an image to be added with unique information and a type of unique information to be added to the image. The unique information selection pattern is, for example, a table T1 shown in FIG. 4 in which each frame number is associated with information on whether unique information is required to be transmitted and the type of unique information to be transmitted. The unique information selection pattern is stored in the storage unit 24. The control unit 21 refers to the table T1 stored in the storage unit 24, and selects an image to be added with unique information and types of unique information to be added to the image.

When the imaging unit 22 outputs an image to be added with unique information, the signal processing unit 23 performs the following under the control of the control unit 21: performing the predetermined processing on the image data; obtaining unique information of the selected type to be added to the image data from the storage unit 24 or the imaging unit 22; generating a unique information line to which the obtained unique information is added after an identification signal ID; adding the unique information subsequent to the identification signal ID to the image data; and outputting the image data to the communication processing unit 25.

Figure 4:
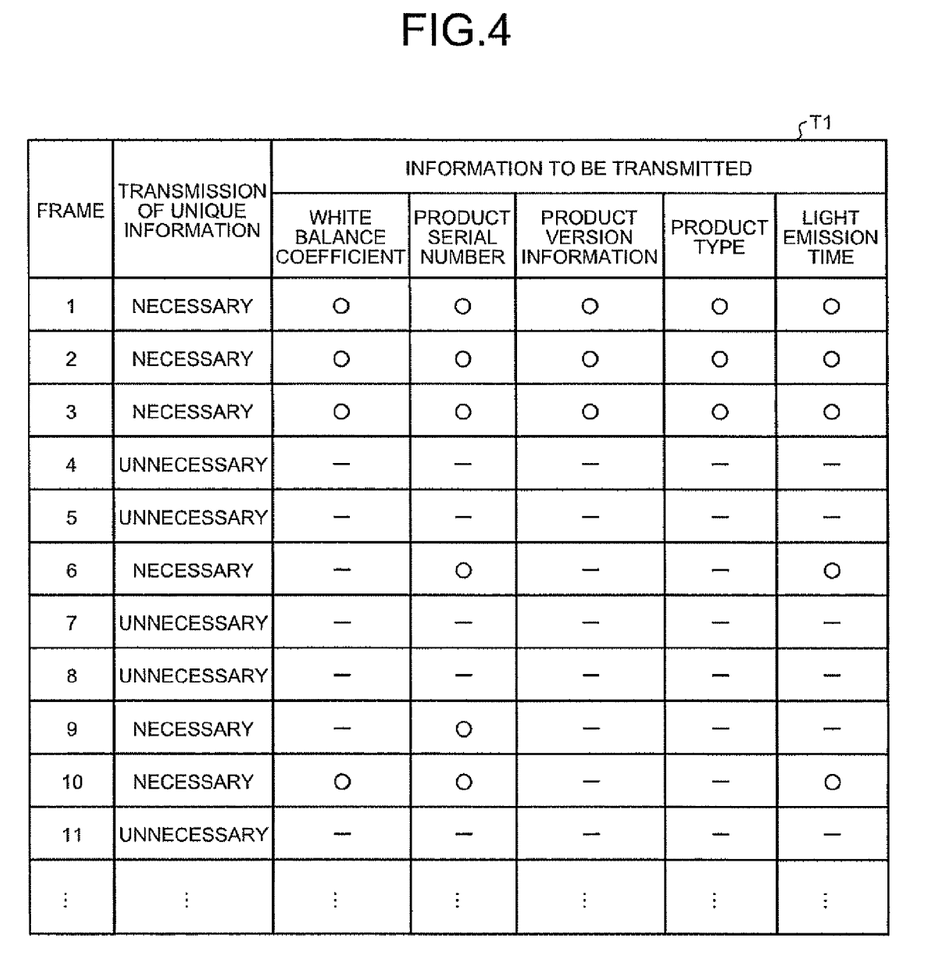
FIG. 4 is a table of an example of a transmission pattern stored in a storage unit shown in FIG. 2.

For example, if the transmission pattern of the table T1 exemplarily shown in FIG. 4 is referred, the control unit 21 selects the white balance coefficient, the product serial number, the product version information, the product type information, and the LED emission time are selected as unique information about the images of the frame numbers 1 to 3. The white balance coefficient, the product serial number, the product version information, the product type information, and the LED emission time are added to the image data of each of the frame numbers 1 to 3 as a unique information line in which an identification signal ID is added in front of the unique information, and the capsule endoscope 2 transmits the image data added with the unique information. Because transmission of unique information is unnecessary regarding the image data of the frame numbers 4 and 5, the capsule endoscope 2 transmits the image data without unique information. The control unit 21 selects the product serial number and the LED emission time as unique information about the image data of the frame number 6. The product serial number and the LED emission time are added to the image data of the frame number 6 as a unique information line in which a front identification signal ID is added in front of the unique information, and the image data added with the unique information is transmitted from the capsule endoscope 2. Because transmission of unique information is unnecessary regarding the image data of the frame numbers 7 and 8, the capsule endoscope 2 transmits the image data without unique information. The product serial number is selected as unique information about the image data of the frame number 9. The product serial number is added to the image data of the frame number 9 as a unique information line in which an identification signal ID is added in front of the unique information and the capsule endoscope 2 transmits the image data added with the identification information. The white balance coefficient, the product serial number, and the LED emission time are selected as unique information about the image data of the frame number 10. The white balance coefficient, the product serial number, and the LED emission time are added to the image data of the frame number 10 as a unique information line in which the front identification signal ID is added in front of the unique information and the capsule endoscope 2 transmits the image data added with the unique information. Because transmission of unique information is unnecessary regarding the image data of the frame number 11, the capsule endoscope 2 transmits the image data without unique information.

Figure 5:
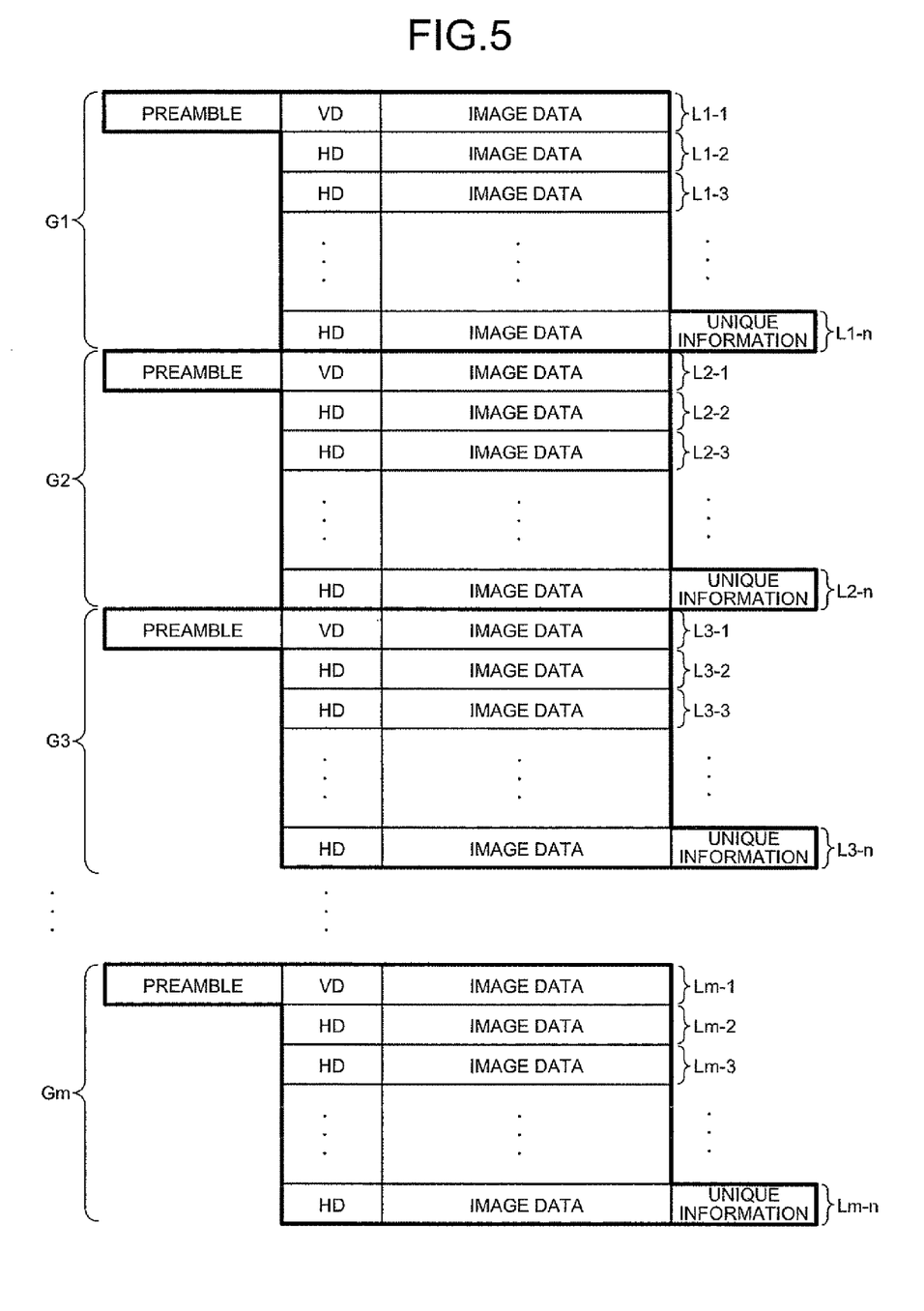
FIG. 5 is a diagram for explaining image signals transmitted from a conventional capsule endoscope.

A conventional capsule endoscope adds all types of unique information to the last line data of image data of each frame, transmits the image data with the all types of unique information. Specifically, as shown in FIG. 5, the last line data L1-n, L2-n, L3-n, and Lm-n among the scanning line data L1-1 to L1-n, L2-1 to L2-n, L3-1 to L3-n, and Lm-1 to Lm-n of the images G1 to Gm are added with unique information, and the image data with the unique information is transmitted. Therefore, the processing unit of the last line data of the image data is longer than that of other line data, and the image components and the unique information components of the image data are sequentially transmitted. As a result, a receiving apparatus has to perform complicated processing for separating the image components from the unique information components while recognizing which image components or unique information components each signal of the last line data constitutes.

On the other hand, the capsule endoscope 2 according to the first embodiment adds an identification signal, which is written in accordance with positions and a signal sequence rule of a vertical synchronization signal and horizontal synchronization signals arranged as top data of each line data, in front of unique information to be transmitted, and transmits the unique information independently from the line data. Therefore, when a signal to be processed contains an identification signal ID, the receiving apparatus 3 can easily recognizes that the information subsequent to the identification ID is the unique information without recognizing which image components or identification information components each signal consists. This makes it possible to easily and accurately read unique information.

As shown in FIG. 5, the conventional capsule endoscope unnecessarily adds unique information to image data of every frame and transmits the image data added with the unique information. Therefore, reduction in the amount of data to be transmitted by the capsule endoscope is limited, which inhibits extension of the operation time of the capsule endoscope.

On the other hand, the capsule endoscope 2 according to the first embodiment selects image data based on the pre-set pattern, adds only selected unique information from a plurality of types of unique information in accordance with the selected image data to only the selected image data, and transmits the image data added with the unique information. Therefore, not as in the case of the conventional endoscope, which adds unique information to image data of every frame and transmits the image data added with the unique information, the amount of data to be transmitted can be reduced without reducing the amount of the data about captured images. This leads to power reduction, and, if a battery of the same capacity as that of the conventional endoscope is mounted on the capsule endoscope 2, the operation time can be extended. Furthermore, because the capsule endoscope 2 can reduce the amount of data to be transmitted, the communication time can be shortened, which achieves high-speed communication processing compared with the conventional method.

Furthermore, in the first embodiment, because setting for adding unique information is performed in accordance with the contents of the image processing performed by the receiving apparatus, no error is caused in the image processing performed by the receiving apparatus.

For example, regarding the white balance coefficient, it suffices if the receiving apparatus 3 receives the accurate white balance coefficient once. However, transmitting of the white balance coefficient only once cannot assuredly exclude the influence caused when an error is caused in data exchange. For this reason, the capsule endoscope 2 transmits the white balance coefficient for multiple times required for check processing on the white balance coefficient. For example, after transmitting image data of 10 frames with the white balance coefficients and identification ids of the image data for the check processing for the white balance coefficient, the white balance coefficient is transmitted for each 10 frames. The receiving apparatus 3 checks each of the white balance coefficients added to the image data of the 10 frames, thereby obtaining the correct white balances. Furthermore, the capsule endoscope 2 can check whether the obtained coefficient is correct using the white balance coefficient transmitted for each 10 frames. The product serial number is used by the receiving apparatus to identify received image data and determine whether the image data is transmitted from the capsule endoscope 2. Therefore, the capsule endoscope 2 adds the product serial numbers to image data for, for example, each two frames and transmits the image data added with the product serial number. By checking the product serial number transmitted for each two frames with the previously received product serial number, the receiving apparatus 3 can proceed the image processing while determine whether the image data is transmitted from the capsule endoscope 2. In this manner, in the first embodiment, because setting for adding unique information is performed based on the contents of the image processing performed by the receiving apparatus, the receiving apparatus can perform the image processing smoothly without errors in the image processing performed by the image receiving apparatus.

When unique information is not added to image data contained in a received wireless signal, the receiving apparatus 3 adds, to the image data, the unique information added to the image data most recently received among previously-received image data added with unique information, and stores the unique information, thereby preventing errors in the image processing performed by the processing apparatus 4.

Figure 6:
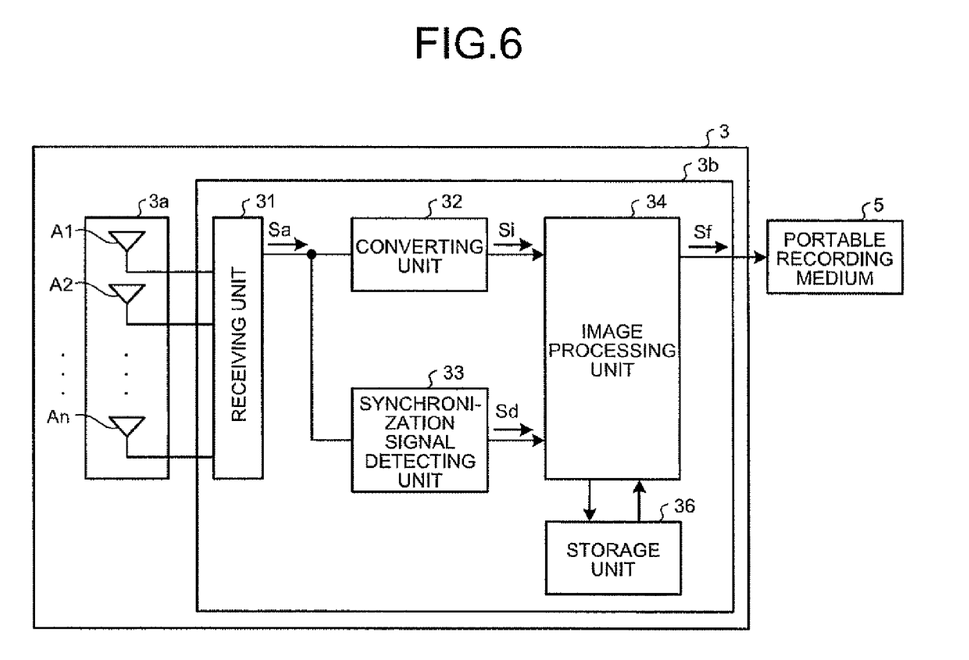
FIG. 6 is a block diagram of a configuration of a receiving apparatus shown in FIG. 1.

The receiving apparatus 3 shown in FIG. 1 is explained in detail below. As shown in FIG. 6, the receiving apparatus 3 includes the wireless unit 3a and the receiving main unit 3b. The receiving main unit 3b includes a receiving unit 31, a converting unit 32, a synchronization signal detecting unit 33, an image processing unit 34, and a storage unit 36. The receiving unit 31 switches between antennas A1 to An, and receives a wireless signal via the switched antenna. The receiving unit 31 performs receiving processing including modulation and analog/digital conversion, and outputs a signal Sa. The converting unit 32 converts the signal Sa received from the receiving unit 31 to a signal Si in a signal format processable by the image processing unit 34. The converting unit 32 outputs the signal Si in synchronization with timing at which the synchronization signal detecting unit 33 output synchronization signal information. The synchronization signal detecting unit 33 detects various types of synchronization signals VD, HD, and ID from the signal Sa, and outputs a synchronization signal information Sd about the detected synchronization signals to the image processing unit 34. The image processing unit 34 performs predetermined processing on the signal Si output from the converting unit 32, and outputs image data Sf corresponding to an image of one frame. The storage unit 36 stores therein information necessary for image processing performed by the receiving apparatus 3. In addition to the signal sequences of the vertical synchronization signal and the horizontal synchronization signals, the storage unit 36 stores therein the signal sequence of the signal ID, and the unique information added to the image data.

When unique information is not added to image data to be processed, the image processing unit 34 obtains the unique information added to the image data most recently received among previously-received image data added with unique information, adds the obtained unique information to the image data to be processed, and stores the unique information in the portable recording medium 5.

Figure 7:
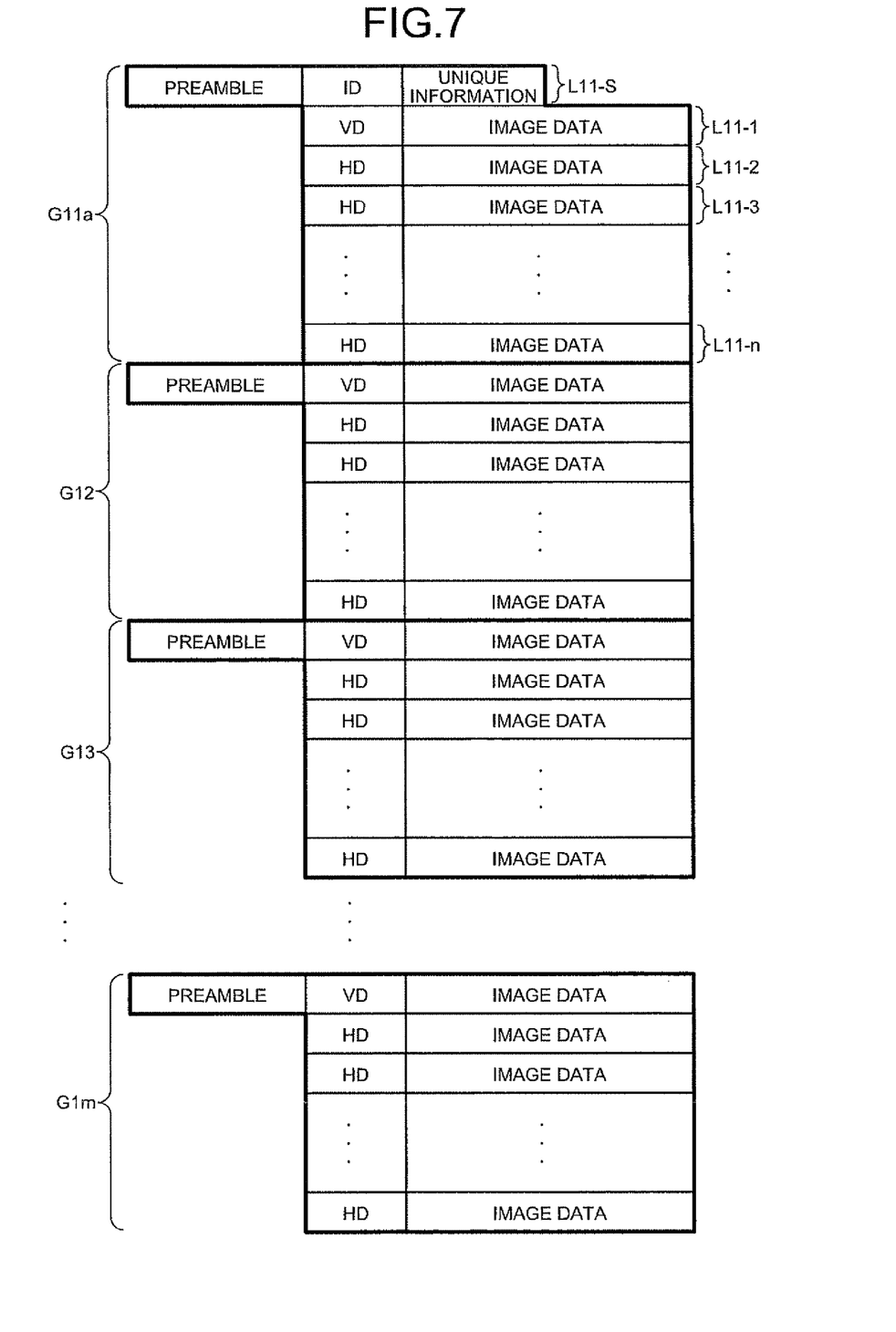
FIG. 7 is a diagram for explaining image signals transmitted from the capsule endoscope shown in FIG. 1.
Figure 8:
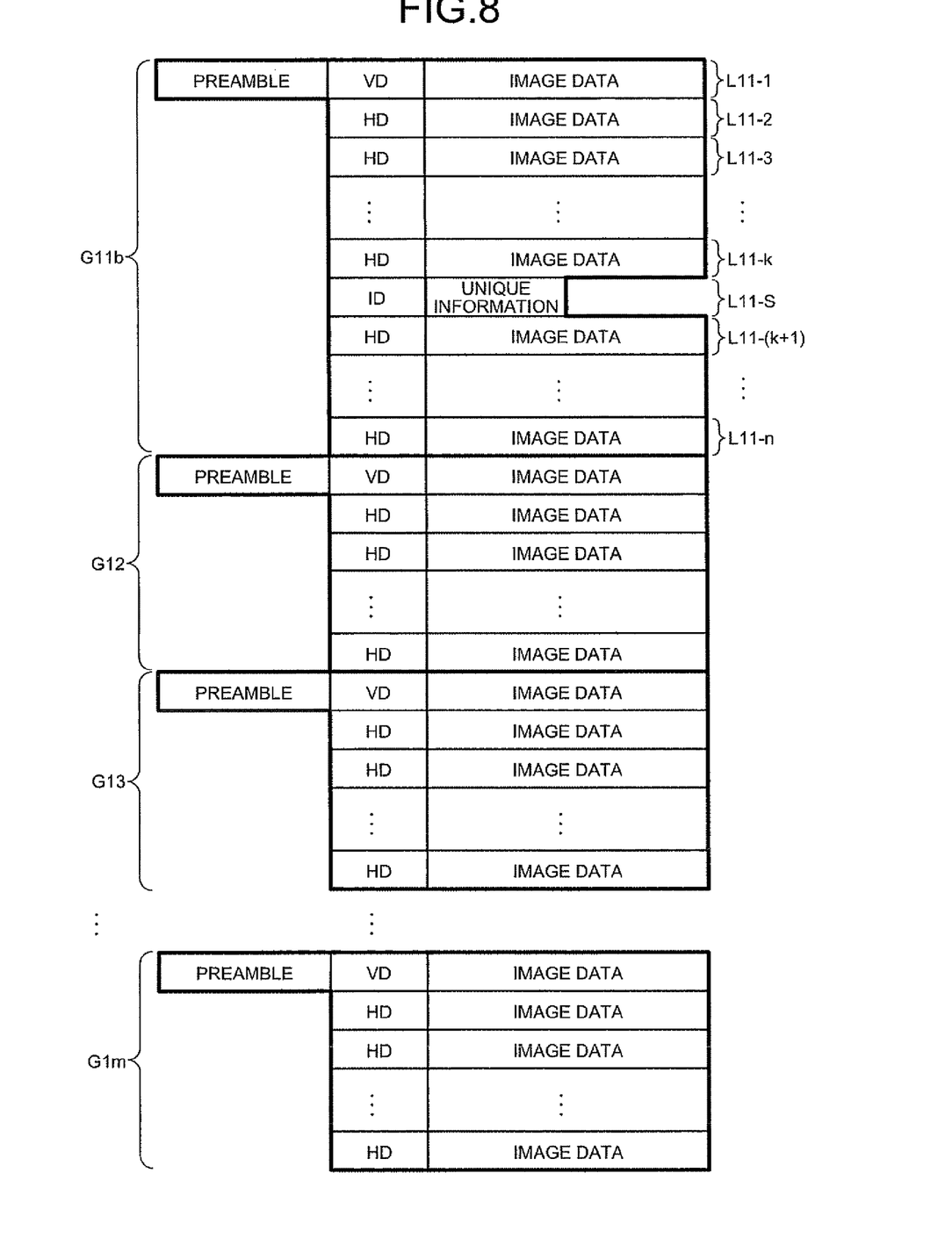
FIG. 8 is a diagram for explaining image signals transmitted from the capsule endoscope shown in FIG. 1.

Because the receiving apparatus 3 recognizes that the information subsequent to the synchronization signal is the unique information corresponding to the image data depending on the identification signal ID, the receiving apparatus 3 can recognize the unique information as long as the identification ID is arranged in front of the unique information. For this reason, the unique information line L11-S exemplarily shown in FIG. 3 is not necessarily added to the end of the image data. For example, as shown in FIG. 7, the unique information line L11-S can be added in front of the top line data L11-1 of an image G11a. Alternatively, as shown in FIG. 8, the unique information line L11-S can be added between the middle line data L11-k and L11-(k+1) of an image G11b.

Figure 9:
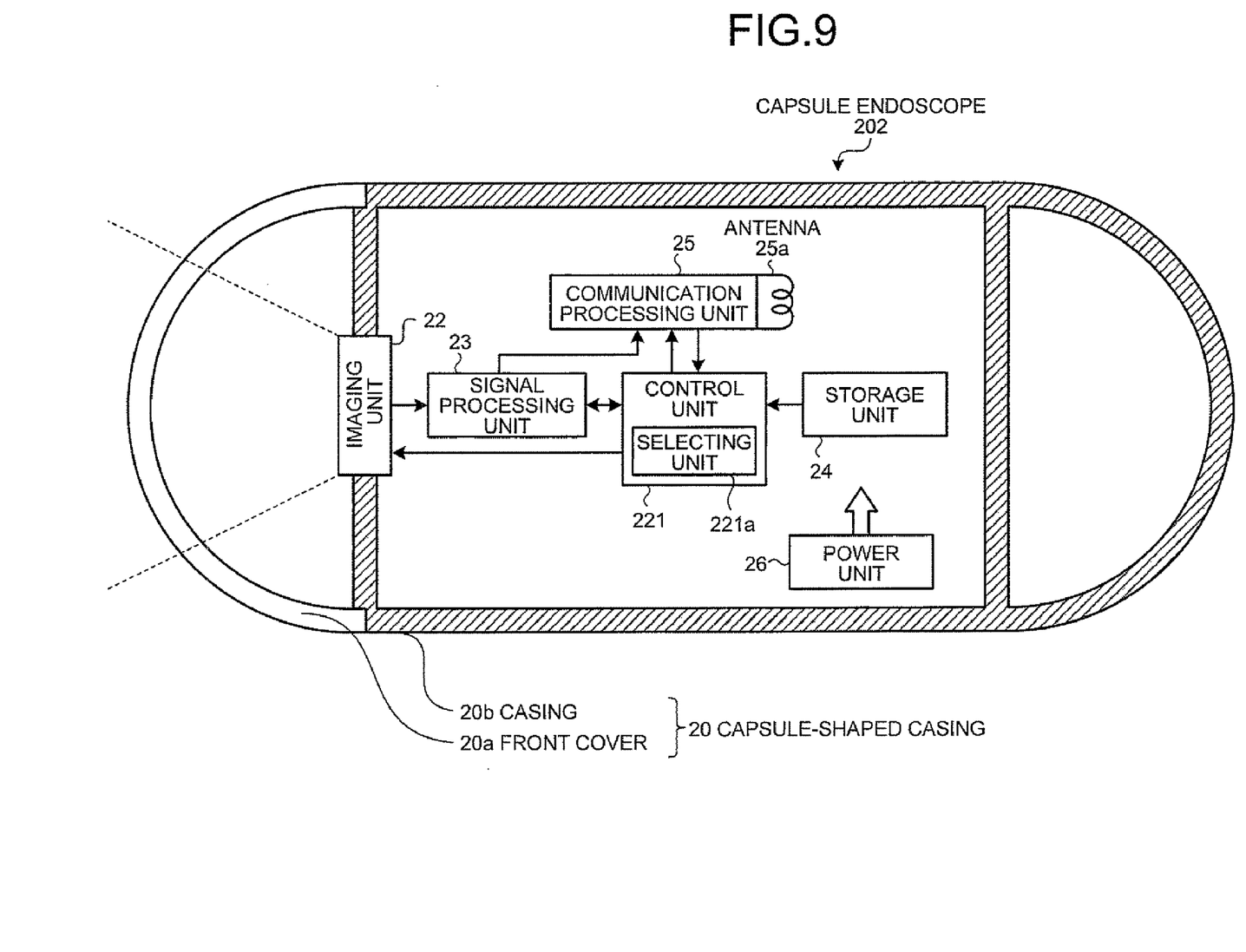
FIG. 9 is a block diagram of a configuration of a capsule endoscope according to a second embodiment of the present invention.

An in-vivo information acquiring system according to a second embodiment of the present invention is explained below. The in-vivo information acquiring system according to the second embodiment includes a capsule endoscope 202 shown in FIG. 9 instead of the capsule endoscope 2 shown in FIG. 2. As shown in FIG. 9, the capsule endoscope 202 includes, instead of the control unit 21 shown in FIG. 2, a control unit 221 that includes a selecting unit 221a that selects image data to be added with unique information.

The selecting unit 221a selects image data to be added with unique information in accordance with the operation status of the imaging unit 22. The selecting unit 221a selects the image data to be added with unique information based on a time during which an LED of the imaging unit emits light per image. As in the case of the first embodiment, the signal processing unit 23 adds unique information to the image data after an identification signal ID, and outputs the image data added with the unique information to the communication processing unit 25.

Figure 10:
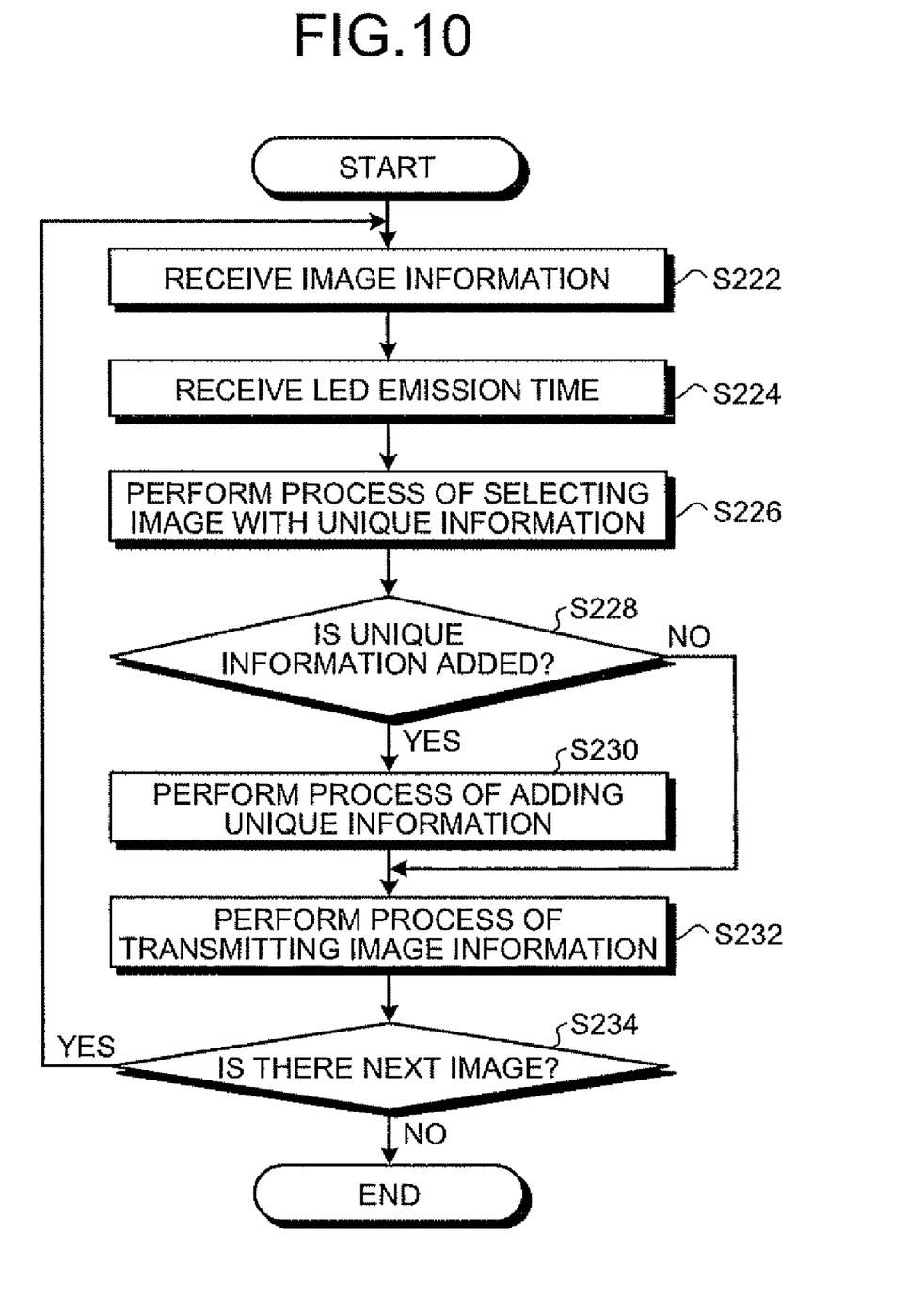
FIG. 10 is a flowchart of a process procedure of processing for selecting an image to be added with unique information, which is performed by the capsule endoscope shown in FIG. 9.

Processing for selecting an image to be added with unique information, which is performed by the capsule endoscope 202, is explained below with reference to FIG. 10. The signal processing unit 23 receives image information containing an image captured by the imaging unit 22 (step S222), receives the LED emission time required for capturing the images (step S224), and outputs the LED light emission time to the control unit 221. Based on the LED emission time output by the signal processing unit 23, the selecting unit 221a performs unique-information-adding-image selection processing in which it is determined whether to select the image data corresponding to the LED emission time as an image to be added with unique information including the LED emission time (step S226) and outputs the result of determination to the signal processing unit 23. The signal processing unit 23 determines whether the image is selected by the selecting unit 221a as an image to be added with unique information (step S228). When the image is selected as an image to be added with unique information (YES at step S228), the signal processing unit 23 performs unique information adding processing in which predetermined unique information including the LED emission time is added after the identification signal ID and added to the image data (step S230), and outputs the processed image data to the communication processing unit 25.

On the other hand, when the image is not selected as an image be added with unique information (NO at step S228), the signal processing unit 23 performs predetermined processing on the image without adding unique information, and outputs the image to the communication processing unit 25. The communication processing unit 25 performs image information transmission processing for transmitting the image data, which is received from the signal processing unit 23, via the antenna 25a (step S232). The communication processing unit 25 determines whether there is the next image (step S234). When there is the next image (YES at step S234), the process goes back to step S222 and each processing is performed on the next image. On the other hand, when there is no next image to be processed (NO at step S234), the processing on the image is completed.

Examples of the unique-information-adding-image selection processing performed by the selecting unit 221a are explained below. When the LED emission time varies from the LED emission time required for capturing the previous image by a predetermined value or more, the selecting unit 221a selects the image data for which the LED emission time varies as image data to be added with unique information.

Figure 11:
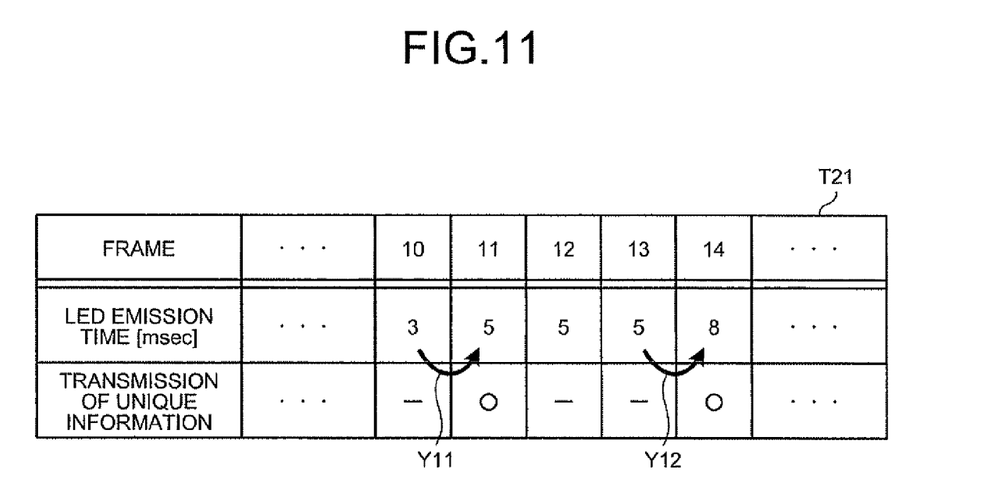
FIG. 11 is a diagram for explaining the processing for selecting an image to be added with unique information, which is performed by the capsule endoscope shown in FIG. 9.

An example is explained below in which setting is performed such that unique information is added to image data and the image data added with the unique information is transmitted if the LED emission time varies by at least 2 milliseconds from that required for capturing the last previous image as, for example, the case shown in a table T21 of FIG. 11 in which the LED emission time varies from 3 milliseconds at the 10th frame, to 5 milliseconds at the 11th frame, and to 8 milliseconds at the 14th frame. In the case of FIG. 11, as indicted by the arrows Y11 and Y12, the LED emission times required for the 11th and 14th frames vary respectively from those required for capturing the respective last previous images by at least 2 milliseconds. Therefore, the capsule endoscope 202 adds the LED emission times "5 milliseconds" and "8 milliseconds" as unique information using identification signals ID respectively to the image data of the 11th frame and the image data of the 14th frame, and transmits the image data added with the unique information.

Figure 12:
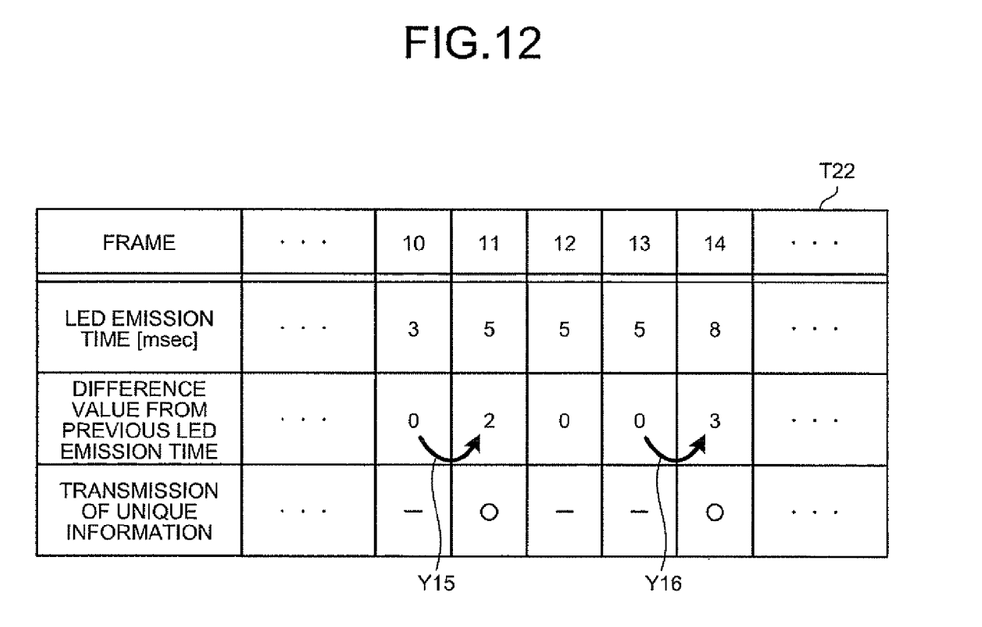
FIG. 12 is a diagram for explaining the processing for selecting an image to be added with unique information, which is performed by the capsule endoscope shown in FIG. 9.

Instead of an absolute value of the LED emission time varying from that required for capturing the last previous image by at least the predetermined value, the capsule endoscope 202 can transmit, as unique information, a difference value between the LED emission time and that required for capturing the last previous image. For example, if setting is performed such that unique information is added to image data and the image data added with the unique information is transmitted when the LED emission time varies by at least 2 milliseconds from that required for capturing the last previous image, the capsule endoscope 202 regards, as unique information, the difference values "2 milliseconds" and "3 milliseconds" between the LED emission time and the LED emission time required for capturing the last previous images represented by the arrows Y15 and Y16 shown in FIG. 12. The capsule endoscope 202 adds the unique information and identification signals ID to the image data of the 11th and 14th frames, and transmits the image data added with the unique information.

Alternatively, the capsule endoscope 202 can determine whether the LED emission time varies to a value below or over a predetermined threshold to select image data to be added with an LED emission time as unique information. The case where the predetermined threshold is 8 milliseconds is explained below as an example. When there is image data for which the LED emission time varies to a value above 8 milliseconds, the capsule endoscope 202 adds a signal "1" representing that the LED emission time is over the predetermined threshold as unique information to the image data, and transmits the image data added with the unique information. On the other hand, when there is image data for which the LED emission time varies to a value below 8 milliseconds, the capsule endoscope 202 adds, a signal "0" representing that the LED emission time is below the predetermined threshold as unique information to the image data, and transmits the image data added with the signal "0".

As in the case of the first embodiment, when image data contained in a received wireless signal is not added with unique information, the receiving apparatus 3 adds, to the image data, the unique information added to the image data most recently received among previously-received image data added with unique information, and stores the image data added with the unique information. Specifically, in the case represented by the table T21 shown in FIG. 11, the image data of the 12th frame not added with unique information is associated with the unique information added to the image data of the 11th frame, and the image data added with the unique information is stored.

As explained, the capsule endoscope 202 according to the second embodiment selects an image to be added with unique information in association with the point at which the LED emission time varies, adds unique information representing the variation in the LED emission time using the identification signal ID to the selected image data, and transmits the image data added with the unique information, thereby achieving the same effects as those of the first embodiment. Furthermore, when the LED emission time used for calculating a distance to a site to be observed varies, the capsule endoscope 202 transmits information representing the variation in the LED emission time as unique information. Therefore, the processing apparatus 4 smoothly performs each processing for, for example, calculating the distance to the site to be observed using the unique information transmitted from the capsule endoscope 202.

In the first and second embodiments, the case is exemplarily explained where image data captured by the imaging unit 22 is added with unique information such as a white balance coefficient. Alternatively, if the capsule endoscope 2 includes a detecting unit that detects pH of a liquid from the subject 1, the following process can be taken instead of directly adding unique information to pH detection data and transmitting the pH detection data with the unique information. The capsule endoscope 2 additionally arranges an identification signal, which is written in accordance with the signal sequence rule same as that of synchronization signals added in front of the pH detection data, in a position corresponding to the positions in which the synchronization signals are arranged, adds the unique information corresponding to the identification signal after the identification signal, and transmits the pH detection data added with the unique information. This makes it possible to accurately and easily read unique information.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An in-vivo information acquiring system comprising:
  a body-insertable apparatus configured to be introduced into a subject, and to transmit a wireless signal containing an in-vivo image to the outside of the subject; and
  a receiving apparatus configured to receive the wireless signal transmitted from the body-insertable apparatus,
  wherein the body-insertable apparatus is comprised of:
    an imaging unit configured to capture in-vivo images;
    a control unit configured to select an in-vivo image to be added with unique information among the in-vivo images captured by the imaging unit; and
    a transmitting unit configured to additionally arrange an identification signal added to scanning line information about the in-vivo image selected by the control unit, to add unique information relating to the identification signal after the identification signal, and to transmit the in-vivo image added with the unique information,
  wherein when the in-vivo image contained in the wireless signal is not added with unique information, the receiving apparatus adds, to the in-vivo image, unique information added to an in-vivo image most recently received by the receiving apparatus among in-vivo images attached with unique information and previously received by the receiving apparatus, and stores the in-vivo image added with the unique information.

2. The in-vivo information acquiring system according to claim 1, wherein the control unit selects the in-vivo image to be added with the unique information based on a predetermined image selection pattern.

3. The in-vivo information acquiring system according to claim 1, wherein
  the unique information includes plural types of unique information,
  the control unit selects a type of unique information to be added to the in-vivo image selected by the control unit from the types of unique information, and
  the transmitting unit adds the type of unique information selected by the control unit to the in-vivo image selected by the control unit.

4. The in-vivo information acquiring system according to claim 1, wherein the control unit selects the in-vivo image to be added with the unique information in accordance with an operation status of the imaging unit.

5. The in-vivo information acquiring system according to claim 4, wherein the control unit selects the in-vivo image to be added with the unique information based on a time during which a light emitting unit of the imaging unit emits light per image.

* * * * *